(12) United States Patent
Buurman et al.

(10) Patent No.: US 9,465,920 B2
(45) Date of Patent: Oct. 11, 2016

(54) PROVIDING ASSISTANCE WITH REPORTING

(71) Applicant: KONINKLIJKE PHILIPS N.V., Eindhoven (NL)

(72) Inventors: Johannes Buurman, 's-Hertogenbosch (NL); Iwo Willem Oscar Serlie, Best (NL); Zarko Aleksovski, Eindhoven (NL); Rudolph Martherus, Vlissingen (NL)

(73) Assignee: Koninklijke Philips N.V., Eindhoven (NL)

( * ) Notice: Subject to any disclaimer, the term of this patent is extended or adjusted under 35 U.S.C. 154(b) by 8 days.

(21) Appl. No.: 14/402,333

(22) PCT Filed: May 27, 2013

(86) PCT No.: PCT/IB2013/054358
§ 371 (c)(1),
(2) Date: Nov. 20, 2014

(87) PCT Pub. No.: WO2013/179200
PCT Pub. Date: Dec. 5, 2013

(65) Prior Publication Data
US 2015/0142421 A1    May 21, 2015

Related U.S. Application Data

(60) Provisional application No. 61/652,909, filed on May 30, 2012.

(30) Foreign Application Priority Data

May 30, 2012  (EP) .................................... 12170023

(51) Int. Cl.
| G06F 17/00 | (2006.01) |
|---|---|
| G06F 19/00 | (2011.01) |
| G06F 17/22 | (2006.01) |
| G06F 17/24 | (2006.01) |
| G06F 17/28 | (2006.01) |

(52) U.S. Cl.
CPC ....... *G06F 19/3487* (2013.01); *G06F 17/2229* (2013.01); *G06F 17/243* (2013.01); *G06F 17/28* (2013.01)

(58) Field of Classification Search
CPC ...... G06F 17/21; G06F 17/28; G06F 17/243; G06F 3/00
USPC ............................................... 707/802; 704/9
See application file for complete search history.

(56) References Cited

U.S. PATENT DOCUMENTS 7,640,496 B1 * 12/2009 Chaulk .................. G06F 3/067
707/999.102
2005/0273365 A1 * 12/2005 Baumgartner ........ G06F 19/321
705/3

(Continued)

FOREIGN PATENT DOCUMENTS

| WO | 9837478 A2 | 8/1998 |
|---|---|---|
| WO | 9917223 A1 | 4/1999 |

(Continued)

OTHER PUBLICATIONS

Langlotz, C.P. MD, PhD. "Structured Radiology Reporting: Are We There Yet?". Radiology: vol. 253: No. 1, Oct. 2009.

(Continued)

*Primary Examiner* — Daniel Abebe

(57) ABSTRACT

A system for maintaining corresponding information in a structured document and in a report is disclosed. The structured document comprises structured data elements and the report comprises text in a natural language. An associating unit (1) is arranged for associating a structured data element of the structured document with an associated part of the report, wherein information represented by the structured data element corresponds to information represented by the associated part of the report. A determining unit (2) is arranged for determining a change to one of the structured data element and the associated part of the report, to obtain a determined change. A corresponding change unit (3) is arranged for making a corresponding change to the other one of the structured data element and the associated part of the report, based on the determined change.

16 Claims, 2 Drawing Sheets

(56) References Cited

U.S. PATENT DOCUMENTS

2006/0004745 A1* 1/2006 Kuhn .................. G06Q 10/10
2013/0251233 A1* 9/2013 Yang .................. G06T 7/0012
                                                        382/132

FOREIGN PATENT DOCUMENTS

WO    2010109351 A1    9/2010
WO    2011036585 A1    3/2011

OTHER PUBLICATIONS

Channin, D.S. et al. "The Annotation and Image Mark-Up Project". Radiology. radiology.rsna.org, Volumber 253: No. 3—Dec. 2009.

Zimmerman, S.L. MD, et al. "Automated Structured Reporting of Imaging Findings Using the AIM Standard and XML". RadioGraphics vol. 31 Nr 3, 2011; p. 881-887.

Levy, M.A. MD, PhD et al. "Current and Future Trends in Imaging Informatics for Oncology". The Cancer Journal vol. 17 No. 4, Jul./Aug. 2011; p. 203-210.

* cited by examiner

PROVIDING ASSISTANCE WITH REPORTING

CROSS-REFERENCE TO PRIOR APPLICATIONS

This application is the U.S. National Phase application under 35 U.S.C. §371 of International Application No. PCT/IB2013/054358, filed on May 27, 2013, which claims the benefit of U.S. Provisional Application No. 61/652,909, filed on May 30, 2012 and European Patent Application No. 12170023.1, filed on May 30, 3012. These applications are hereby incorporated by reference herein.

FIELD OF THE INVENTION

The invention relates to providing assistance with reporting.

BACKGROUND OF THE INVENTION

In healthcare, Clinical Decision Support (CDS) systems are used for processing radiology information and as an aid to create accurate and complete reporting.

In radiology (and in many other medical disciplines), reports are produced to document what was found, including an impressions and recommendations section. Such reports may serve several functions: communication to the referring physician, billing, documentation for own use. When a patient returns for a follow-up examination, the report may have to be read again. Also, for management reporting or medical research, there is a desire to do statistics over cases. This is a different use of the same report.

Radiology reporting may be performed using dictation. The dictated words may be transcribed manually and/or using automatic speech recognition. The report that is created has an unstructured text, optionally with a number of sections and paragraphs. Systems that produce a report with machine readable structure are also known. The paper "Automated Structured Reporting of Imaging Findings Using the AIM Standard and XML", by S. L. Zimmerman et al., in RadioGraphics 2011; 31:881-887, published online doi:10.1148/rg.313105195, discloses a system that provides a mouse-keyboard interface to allow a radiologist to enter details into a report. The advantage of a structured representation is that different renderings of the report can be produced for different recipients: e.g. an oncologist (interested in disease progression) may get a different report than a surgeon (interested in surgical options), which is again different from the reports for a general practitioner or a patient.

Sometimes the report is drafted based on a template. This still results in unstructured text, although the format, content and terminology has been standardized to an extent.

An important purpose of radiology is to answer the clinical question asked by a referring physician by means of a radiology request. In today's radiology workflow, images may be read and reports may be prepared, dictated, revised, and approved by different people. Furthermore, reporting efforts include preparing the presentation or conferencing of the patient case, because communicating radiological findings is as important as the rendering of interpretation.

SUMMARY OF THE INVENTION

It would be advantageous to have improved assistance with reporting. To better address this concern, a first aspect of the invention provides a system comprising an associating unit for associating a structured data element of a structured document with an associated part of a report, wherein the report comprises text in a natural language, and wherein information represented by the structured data element corresponds to information represented by the associated part of the report;

a determining unit for determining a change to one of the structured data element and the associated part of the report, to obtain a determined change; and a corresponding change unit for making a corresponding change to the other one of the structured data element and the associated part of the report, based on the determined change.

The system can be used to maintain corresponding information in a structured document and in a report. Because the change to the one of the structured document and the report is also applied to the other, the information in both representations is kept similar. This way, the user can focus on one representation and make changes thereto, without the information contained in the two representations diverging. This improves the consistency of the data. For example, the user can make changes to the report in natural language, without worrying about updating the corresponding structured data element, because the latter is updated automatically. The same may be done the other way round. If a structured data element is changed, a corresponding change is automatically made to the report in natural language.

Using these techniques, the user can choose which representation the user wants to work with. Consequently, it does not make necessary undesired changes to the way of working.

The information represented by the structured data element or the information represented by the associated part of the report may be associated with a specific image dataset. This allows the annotation of the specific image dataset and creating a report in respect of the specific image dataset. Moreover, it provides a context that helps to interpret the structured document and the report. This feature may be useful in radiology reporting.

The system may comprise a first cursor unit for determining a first cursor position in one of the structured document and the report, and a second cursor unit for determining a second cursor position in the other one of the structured document and the report, wherein the first cursor position and the second cursor position point to the structured data element and the associated part of the report. This allows the system to find the corresponding positions, by means of the cursor positions. Moreover, the user can be presented with an indication of the corresponding cursor positions, for example by means of a visualization. This helps the user to identify corresponding portions of the structured document and the report. Moreover, the user may be allowed to change the position of the cursor in one representation, wherein the second cursor unit may be arranged to automatically change the cursor to a corresponding position in the other representation. When the cursors have reached the desired position, the user may make the change in either representation, which may then be automatically updated in the other representation by the corresponding change unit. This improves the predictability of the behavior of the system.

The determining unit may comprise a first insert unit for inserting a representation of information into the one of the structured data element of the structured document and the associated part of the report. The corresponding change unit may comprise a second insert unit for inserting a corresponding representation of information into the other one of the structured data element and the associated part of the report. This allows to add information to both representations in an efficient manner, while maintaining the consistency between both representations.

The representation of information inserted into the structured data element of the structured document may comprise a text field of the structured data element with text comprising at least part of the representation of information inserted into the associated part of the report. This can be used to support insertion of any text into both representations, without limiting the freedom of expression to a predetermined lexicon. This way, users do not have to restrict their expression capabilities to pre-defined options, because they can provide any words in both the structured document and the report.

The system may comprise a copy preparation unit for determining at least one of a to-be-copied structured data element of the structured document and a to-be-copied part of the report. The system may further comprise a copy execution unit for inserting a corresponding representation of information into the other one of the structured document and the report, wherein the corresponding representation of information corresponds to information represented by said at least one of the to-be-copied structured data element and the to-be-copied part of the report. The associating unit may be arranged for associating said at least one of the to-be-copied structured data element of the structured document and the to-be-copied part of the report with the corresponding representation inserted into the other one of the structured document and the report. Consequently, a change to either the original or the copied representation may be correspondingly made to the other representation. This allows a user to selectively copy parts from one representation into the other representation. These copied parts then become associated with their originals. When subsequently a change is made to either representation, the other representation is kept up-to-date by making a corresponding change. This helps to keep the representations consistent.

The associating unit may be arranged for associating a plurality of structured data elements of the structured document with associated parts of the report, to obtain a correspondence mapping. This way, the associations are ready to be used whenever a change is made. This improves the efficiency of the system, because at the time a change is made, the associated part is readily available in the correspondence mapping.

The structured data element may represent a standard term by means of a code. This enhances the structure of the structured document, because standard terms may be used. Moreover, it allows to offer the user help in editing the structured document because appropriate suggestions from the standard terms may be given.

In another aspect, the invention provides a workstation comprising a system set forth.

In another aspect, the invention provides a method of providing assistance with reporting, the method comprising
associating a structured data element of a structured document with an associated part of a report, wherein the report comprises text in a natural language, and wherein information represented by the structured data element corresponds to information represented by the associated part of the report;
determining a change to one of the structured data element and the associated part of the report, to obtain a determined change; and
making a corresponding change to the other one of the structured data element and the associated part of the report, based on the determined change.

In another aspect, the invention provides a computer program product comprising instructions for causing a processor system to perform the method set forth.

It will be appreciated by those skilled in the art that two or more of the above-mentioned embodiments, implementations, and/or aspects of the invention may be combined in any way deemed useful.

Modifications and variations of the workstation, the system, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated hereinafter with reference to the drawings.

DETAILED DESCRIPTION OF EMBODIMENTS

Figure 1:
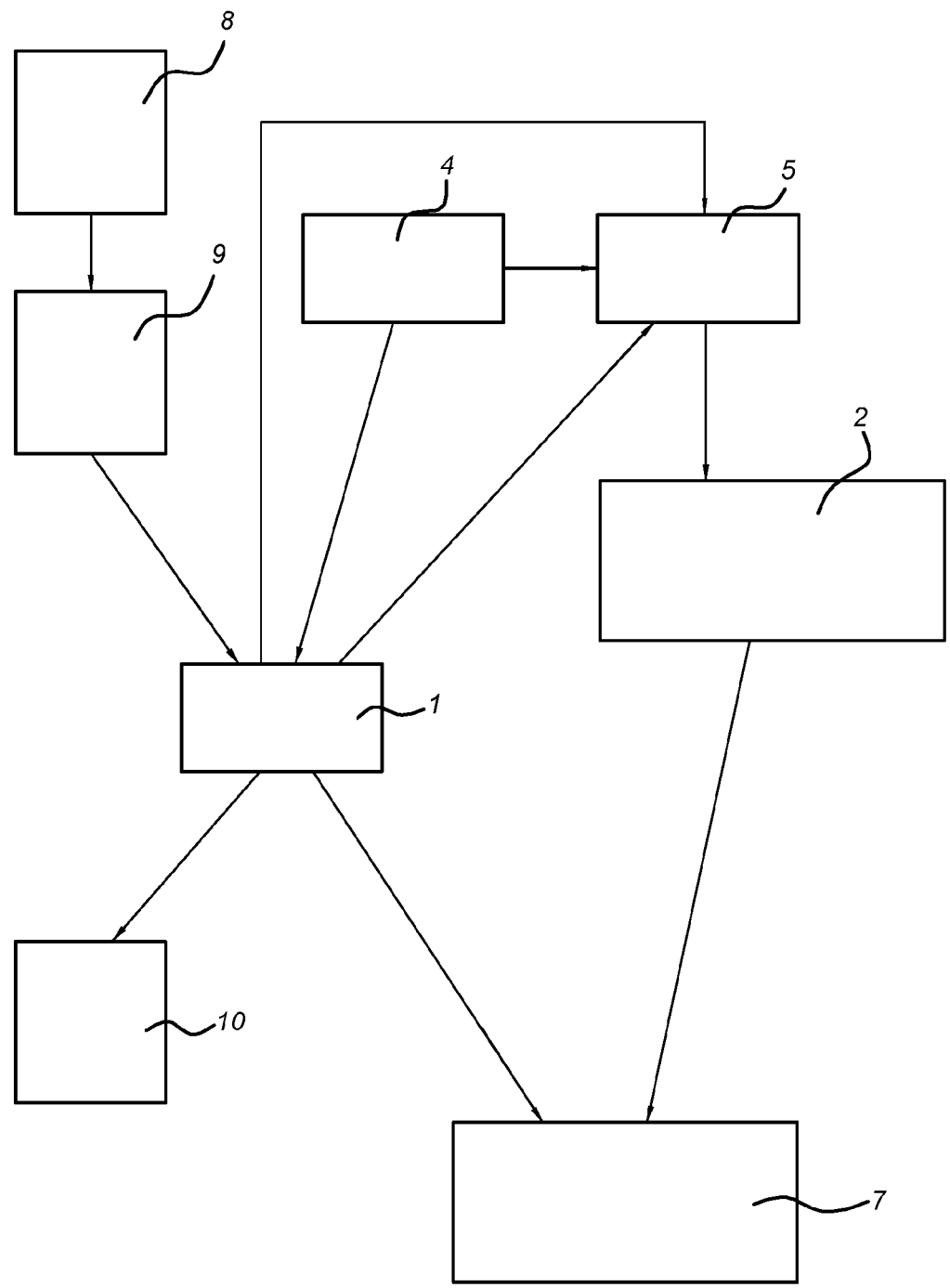
FIG. 1 is a block diagram illustrating aspects of a system that provides assistance with reporting.

FIG. 1 illustrates a system for providing assistance in reporting. The system is capable of maintaining corresponding information in a structured document and in a report. The structured document comprises structured data elements and the report comprises text in a natural language. The system may be implemented as part of a document processing system, such as a database system or a healthcare information system or picture archiving and communications system. The system may also be implemented as a standalone workstation. The system may also be implemented using dedicated electronic circuitry. The system may have access to a communication port to transmit and/or receive data, such as documents and images. To that effect, the communications port may be connected to a network. Moreover, the system may comprise user interface devices such as a mouse, keyboard, microphone with speech recognition, or touch screen. These devices may be used to enable a user to control the system and to provide the contents of a structured document or a free text report. A display device may be provided to display the contents of reports, show cursor positions and control buttons.

The system may comprise an associating unit 1 arranged for associating a structured data element of the structured document with an associated part of the report. Hereinafter, the term representation may be used to denote either one of a structured document or a report. The report, as used herein, may comprise free text. For example, it is a freely editable text document that may be formatted with boldface and italics and the like. Moreover, the report may comprise sections. Those sections may be freely configurable or may be enforced by the system. The information represented by the structured data element may correspond to information represented by the associated part of the report. Such a part may be a sentence, a word, a number, a paragraph, or any part of the report. The association may be established in many different ways. For example, if one representation is automatically generated from the other representation, the associations may be generated and stored at the time of generation. Alternatively, the associating unit 1 may be arranged for scanning the other representation to find a portion representing corresponding information. The associating 1 unit may start from the structured data element of the structured document and determine the associated part of the report. Alternatively, the associating unit 1 may start from the report and determine that a part of the report is associated with a structured data element of the structured document, because the structured data element represents corresponding information.

The associating unit 1 may be arranged for associating a structured data element with a plurality of parts of the report. For example, the same information may appear in a plurality of places in the report. For example, some of the information in one of the main sections of the report may be repeated in a Conclusions section. Both these appearances of the same information may be associated with the same structured data element. If the structured data element changes, the different associated parts of the report may be updated to reflect the change. Similarly, the associating unit 1 may be arranged for associating a plurality of data elements with the same part of the report.

The system may comprise a determining unit 2 arranged for determining a change to one of the structured data element and the associated part of the report, to obtain a determined change. This determining unit 2 may be an observation unit that simply detects that a change has been made or is being made. To this end, the determining unit 2 may be operatively coupled to other parts of the system. Those other parts of the system may be arranged for sending a signal to the determining unit 2 when a change is made. The determining unit 2 may also be arranged for periodically checking whether a change has been made. Alternatively, the determining unit 2 may be arranged for actively making the change. For example, the determining unit 2 is controlled by the user through a user interface.

The system may comprise a corresponding change unit 3 arranged for making a corresponding change to the other one of the structured data element and the associated part of the report, based on the determined change. In case the determining unit 2 detected a change to the structured data element of the structured document, the corresponding change unit 3 is arranged for making a corresponding change to the associated part of the report. In case the determining unit 2 detected a change to the associated part of the report, the corresponding change unit is arranged for making a corresponding change to the structured data element of the structured document. Detailed examples of how to change the other one of the representations, are given elsewhere in this description.

The information represented by the structured data element or the information represented by the associated part of the report may be associated with a specific image dataset. For example, the documents may contain an identification or a link to the specific image dataset. For example, the system comprises an image viewer for displaying the image, and allow simultaneously the user to create or edit the structured document and/or the report. The structured document and/or report thus created, may be stored in a database with an association with the image dataset. It is also possible that different structured data elements are associated with different image datasets. It is also possible that different parts of the report are associated with different image datasets.

The system may comprise a first cursor unit 4 for determining a first cursor position in one of the structured document and the report. For example, the cursor position may be determined in a displayed representation of the structured document or report by means of cursor keys or by means of a mouse pointer or touch screen. Alternatively, the cursor position may be determined automatically by the first cursor unit, for example using a predetermined order in which information is input by the user.

The system may comprise a second cursor unit 5 for determining a second cursor position in the other one of the structured document and the report, wherein the first cursor position and the second cursor position point to the structured data element and the associated part of the report. The system can maintain a plurality of structured data elements with their associated parts of the report. The user may be enabled to position a cursor in either of the representations, using the first cursor unit. The second cursor unit then uses the association and the position of the cursor obtained from the first cursor unit, to determine the corresponding cursor position in the other representation.

In case the user uses the first cursor unit 4 to position the cursor to point to some part of the report, the second cursor unit 5 finds out with which structured data element of the structured document said "some part" is associated. This may be done using an explicitly stored table of associations. Alternatively, this may be done by analyzing and processing the structured document and the report, to find corresponding information in both representations.

Similarly, in case the user uses the first cursor unit 4 to position the cursor to point to a structured data element of the structured report, the second cursor unit 5 may find out with which part of the report that structured data element is associated.

The system may also support only one way conversion, so it is possible that the first cursor unit 4 only supports determining the first cursor position in the report. Alternatively, the first cursor unit 4 may support only determining the first cursor position in the structured document.

The determining unit 2 may comprise a first insert unit 6 for inserting a representation of information into the one of the structured data element of the structured document and the associated part of the report. Accordingly, the change determined by the determining unit 2 may involve this inserted representation of information.

Accordingly, the corresponding change unit 3 may comprise a second insert unit 7 for inserting a corresponding representation of information into the other one of the structured data element and the associated part of the report. The second insert unit 7 may comprise a converter that converts the inserted representation into a format that is suitable for the other one of the structured data element and the associated part of the report. When the original is a part of the report, natural language processing and interpretation may be applied to convert the inserted information into one or more structured data elements, which may be inserted into the structured document by the second insert unit 7. When the original, inserted by the first insert unit 6, is a structured data element, the converter may apply natural language generation to generate a piece of natural language suitable for insertion into the report.

In case no particular structured data element can be identified in the structural language or expression possibilities used for the structured document, that corresponds to the information that was inserted into the report, then the system may use a free text field as a structured data element. The representation of information inserted into the structured data element of the structured document may comprise a text field of the structured data element with text comprising at least part of the representation of information inserted into the associated part of the report.

The system may comprise a copy preparation unit 8 for determining at least one of a to-be-copied structured data element of the structured document and a to-be-copied part of the report. The copy preparation unit 8 may be coupled to a user interface of the system. For example, the copy preparation unit 8 may enable a user to select a portion of a representation, and select it to be copied into the other representation. This selection may take place by means of a drag-and-drop operation, for example, or by a copy-and-paste operation. The copy preparation unit 8 may be arranged for enabling a user to indicate a position within the structured document or report where the to-be-copied data will be copied into. Alternatively, the copy preparation unit 8 may be arranged for determining the to-be-copied information automatically, based on reporting standards or decision rules, for example. The copy preparation unit 8 may also be arranged for determining the position where the to-be-copied data will be copied automatically, for example based on the kind of information represented by the to-be-copied data or based on a position of the to-be-copied data or a context of the to-be-copied data in the source representation.

The system may comprise a copy execution unit 9 for inserting a corresponding representation of information into the other one of the structured document and the report, wherein the corresponding representation of information corresponds to information represented by said at least one of the to-be-copied structured data element and the to-be-copied part of the report. The copy execution unit 9 may comprise a converter, similar to the converter discussed above.

The associating unit 1 may be arranged for associating said at least one of the to-be-copied structured data element of the structured document and the to-be-copied part of the report with the corresponding representation inserted into the other one of the structured document and the report. This way, when a change to either representation is detected by the determining unit 2, the system is able to make a corresponding change to the other representation by means of the corresponding change unit 3.

It is possible that the copy preparation unit 8 and the copy execution unit 9 allow the insertion of representations of information based on the same to-be-copied structured data elements into different places of the report. When the structured data element changes after the insertion into the report, the system may be arranged for changing each insertion accordingly.

The associating unit 1 may be arranged for associating a plurality of structured data elements of the structured document with associated parts of the report, to obtain a correspondence mapping. For example, whenever the copy execution unit 9 is activated, the resulting association may be stored for later use. Moreover, one representation may be automatically generated from the other representation. During such generation, the associations may be determined more easily, and may be stored for later use by the determining unit 2 and corresponding change unit 3.

The structured data element may represent a standard term by means of a code. Such a standard term may be defined in a lexicon, such as BI-RADS, and have a code, for example a number, associated therewith. To more clearly preserve the intended term, the code may be stored in the structured data element.

Figure 2:
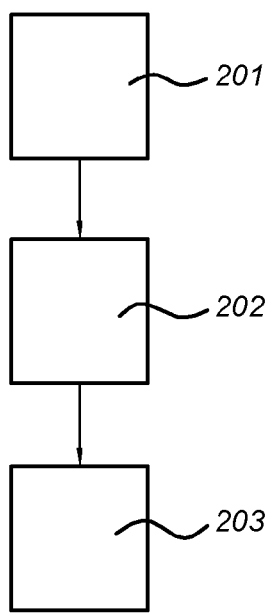
FIG. 2 is a flowchart illustrating aspects of a method of providing assistance with reporting.

FIG. 2 illustrates a method of assisting in reporting. Using the method, it is possible to maintain corresponding information in a structured document and in a report. The method may be applied for radiology reporting, for example. The structured document comprises structured data elements and the report comprises text in a natural language. The method, may comprise a step 201 of associating a structured data element of the structured document with an associated part of the report, wherein information represented by the structured data element corresponds to information represented by the associated part of the report. The method may further comprise step 202 of determining a change to one of the structured data element and the associated part of the report, to obtain a determined change. The method may further comprise a step 203 of making a corresponding change to the other one of the structured data element and the associated part of the report, based on the determined change. The steps do not necessarily be performed in this order. For example, steps 201 and 202 may be exchanged in some embodiments. The method may be implemented by means of a computer program. Moreover, the system described herein may also be implemented at least partly by means of a computer program. The method may be extended and/or modified by the person skilled in the art, based on the description of functionality of the system herein.

The techniques described herein may be applied, for example, to radiology image analysis and reporting systems. For example, they may be applied to systems in which PACS and radiology information system (RIS) are integrated.

A scratch area may be added to the PACS and/or RIS or other image viewing and annotation system, that contains one area where all markings, attention points, collaboration communications and findings with their properties for the patient are collected, before report creation, during a preparation phase. The scratch area may be presented in an organized way from completely unstructured to structured. The information in the scratchpad can then be included in a report, which considerably simplifies the creation of the report itself. The portions of the scratchpad that are included in the report may be linked dynamically with their originals in the scratchpad. This enables a change that was made to an element of the scratchpad to be changed in the report as well. The other way round, when a portion of the report that is linked to the scratchpad is changed, a corresponding change to the scratchpad can be made. This can be realized using the techniques described herein. The scratchpad may function as a bridge between PACS and RIS.

Image observations may be created, described and organized from the start of reading the images by means of a scratchpad. Then, in a later phase, some of the observations recorded in the scratchpad might be described in a report. Some of the markings might be inserted as structured data elements into the report. For example, as elements of a table.

When inserting structured data elements into a report, they may be not inserted as natural language descriptions following a specific preferred reporting style. When considering lesions in the report, the radiologist dictates free text that describes the lesion using the attributes.

After inserting data elements into a report as natural language descriptions, changing the natural language of the report may cause the related structured data items to be changed also. In other words, a live connection between the report and reported items or vice versa may be created. After inserting an item in the report and before confirming the report it might be desired to modify an item or attribute in the report. This should also result in changing related information in the other representation. The techniques described herein may be used to realize this functionality.

When adding information to the report, such as extending descriptions of lesions, the structured source data items may be updated with such extension as well. An example insertion is additional characteristics of lesions. Reporting may contain brief descriptions that adhere to a specific style. Inserting information automatically from a structured representation helps to improve the use of a specific reporting style.

Natural language text in a report may be generated automatically, based on pre-defined lesion properties. In addition, a "live" connection may be preserved between the source information (e.g. in a scratchpad) and target information in the report after inserting an item in the report.

Consider an example in which information is gathered in multiple phases. Structured information might be gathered and manipulated by different persons just after creation of the radiology image and long before the dictation of the report. For example, consider a measurement in an abdominal image. A radiologist may defined it as a target lesion based on the clinical question from the referring physician. In another session, a radiology resident may read the image and defined lesion properties such as "shape=oval", "location=left liver lobe". In a final review, the radiologist may define the liver segment: "segment 4 as part of the left hemiliver". Finally, the radiologist may decide to include the lesion in the report.

When including the lesion into the report, it is possible to select a natural language macro based on the information known of the reported item. The result is a natural language text description of the item based on the lesion information. This may include, but is not limited to type of image, DICOM information, location in image, and lesion properties. In addition to natural language creation, it might be that keywords are used to generate a checklist in a report.

Furthermore, it is possible to preserve the structured information. As a direct consequence, when altering the text in the report, the appropriated lesion properties may be updated as well. This is advantageous when following the lesion in time or using the information for multiple occasions. A 'scratchpad' item or lesion with properties might be used in a diagnostic report and in a tumor board presentation. The radiologist may extend the report with text to further describe findings. It is proposed to extend the related finding information as well.

Hereinafter, a non-limiting example is presented. In the example, a structured document may comprise the following structured data elements: "Lesion 1: Anatomy: liver; Size: 15 mm longest axis; Lobe: left; Segment: 4; Personal keyword: obese."

The corresponding report may have the following text to capture the same information: "Findings section. A mass is present in the segment 4 of the left liver lobe measuring 15 mm in greatest diameter. Impression section. 15 mm liver mass in left lobe."

The report may have been generated from the structured document using natural language generation, for example. Alternatively, the documents may have been made manually. When the user inserts a structured data element "Shape: wedge-shaped" into the structured data element "Lesion 1", the structured document contents is: "Lesion 1: Anatomy: liver; Shape: wedge-shaped; Size: 15 mm longest axis; Lobe: left; Segment: 4; Personal keyword: obese." The system may be arranged for inserting corresponding text into the report, so that the report contents becomes: "Findings section. A wedge-shaped mass is present in the segment 4 of the left liver lobe measuring 15 mm in greatest diameter. Impression section. 15 mm liver mass in left lobe."

Next, the user may change the report, for example using the cursor units described herein, by changing "wedge-shaped" into "oval-shaped", and inserting the location, "along the liver edge", so that the contents of the report becomes: "Findings section. A oval-shaped mass is present in the segment 4 of the left liver lobe located along the liver edge and measuring 15 mm in greatest diameter. Impression section. 15 mm liver mass in left lobe."

Corresponding changes may be made to the structured document, by changing the structured data element "Shape: wedge-shaped" into "Shape: oval-shaped" and inserting new structured data element "On examination: liver edge". The contents of the structured document thus becomes: "Lesion 1: Anatomy: liver; Shape: oval-shaped; Size: 15 mm longest axis; Lobe: left; Segment: 4; Personal keyword: obese; On examination: liver edge."

The system and method described herein may also provide for automatic style formatting. When automatically generated free text is extended by a radiologist with dictated or otherwise edited text, identical style guidelines might be used and natural language text can be structured and re-phrased when appropriately using a set of predefined macro's to stimulate the use of one style.

Information may be captured as early as possible in the radiology workflow and used many times. The structure of information may be preserved independent of the presentation of information. A brief and plain language style may be adhered to when writing reports. Adherence to style guidelines can be stimulated with computer interpretable information.

Using the techniques described herein, reporting may be more quick and accurate. Moreover, efforts and observations of peers in pre-reporting phase may be used in the process.

The proposed method might be implemented by using macro's that map observation properties to natural language descriptions.

Figure 3:
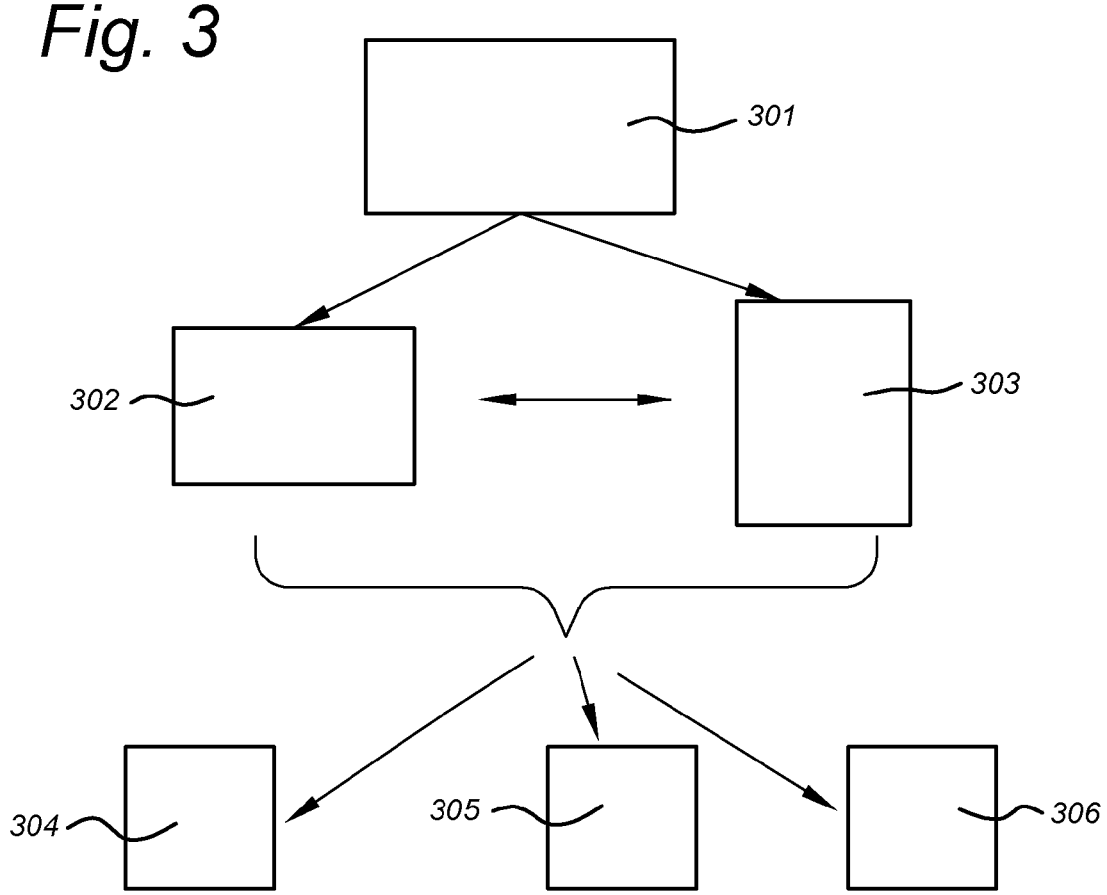
FIG. 3 is a diagram illustrating a context of structured and unstructured documents.

FIG. 3 shows a diagram illustrating an example of reports. Either or both the structured representation 303 of information (or structured document) and the unstructured representation 302 of information (or report) may be initialized from a template 301. For example, templates disclosed by the Radiological Society of North America, Inc. (RSNA) may be used. The structured representation 303 and the unstructured representation 302 may be continuously synchronized in a manner described below. Interaction with both representations may be possible. Interaction with the unstructured representation 302 can be done by means of dictation and speech recognition, or alternatively by typing or cut/copy/paste editing. Interaction with the structured representation 303 can be done by means of e.g. doing a measurement on an image, providing image mark-up or by editing a table. Finally, the output of both representations can be rendered in a way that is specific to the recipient. This can be done for instance using XML, possibly in combination with specific style sheets.

Filling an unstructured text report 302 from a template 301 may be done by speech recognition systems, as known in the art per se. Also the structured representation 303, and a user interface for this, may be derived from a template 301. An important feature of the template 301 is that it should allow free text in (almost) all places, to accommodate unexpected findings and leave freedom for the user. However, this is not a limitation.

Rendering from the structured version to the unstructured version may be done using a structured-to-unstructured style sheet. Initially, the structured-to-unstructured style sheet may be a standard style sheet that can be derived from how the unstructured representation is initialized from the template. If the user changes the formatting (as opposed to the content) of the unstructured representation, the structured-to-unstructured style sheet can automatically be modified to reflect the change. An alternative to this is to limit the formatting options of the user.

Synchronization between the two representations is made possible by the techniques disclosed herein.

If the user changes the unstructured representation 302, the unstructured text may be updated. E.g. if the change is entirely within the value of a template field, then the corresponding item in the structured representation can be updated. An example would be the replacement of the template token "<extent>" by the value "Moderate". In other cases, natural language processing may be used to identify the change. E.g. the sentence "There is a smooth, oval mass at the right 9 o'clock location" might be broken down into an item in the structure and some descriptive attributes. If a textual change cannot be interpreted, the resulting text may be stored as a free text field in the structured document. The structured representation may have free text possibilities everywhere. Finally, if the user has made a change to the formatting, the structured-to-unstructured style sheet may be modified appropriately.

If the user changes the structured representation 303, the unstructured version may be re-rendered using the S2U style sheet. A particular change that is envisioned is the change from a free text finding into a more detailed description. This can be useful if a change in the unstructured text could not be interpreted earlier.

The techniques disclosed herein may be applied in the field of radiology reporting. The techniques may help achieve large-scale adoption of structured reporting in radiology. However, the techniques are not limited thereto. They may also be applied to other medical and non-medical reporting.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a flash drive or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for providing assistance with reporting, comprising
an associating unit for associating a structured data element of a structured document with an associated part of a report, wherein the report comprises text in a natural language, and wherein information represented by the structured data element corresponds to information represented by the associated part of the report;
a determining unit for determining a change to one of the structured data element and the associated part of the report, to obtain a determined change; and
a corresponding change unit for making a corresponding change to the other one of the structured data element and the associated part of the report, based on the determined change,
wherein the determining unit comprises a first insert unit for inserting a representation of information into the one of the structured data element of the structured document and the associated part of the report, and the corresponding change unit comprises a second insert unit for inserting a corresponding representation of information into the other one of the structured data element and the associated part of the report, wherein the second insert unit comprises a converter for converting the inserted representation of information, being a new structured data element, by applying natural language generation to generate a piece of natural language suitable for insertion into the associated part of the report.

2. The system according to claim 1, wherein the information represented by the structured data element or the information represented by the associated part of the report is associated with a specific image dataset.

3. The system according to claim 1, comprising
a first cursor unit for determining a first cursor position in one of the structured document and the report;
a second cursor unit for determining a second cursor position in the other one of the structured document and the report, wherein the first cursor position and the second cursor position point to the structured data element and the associated part of the report.

4. The system according to claim 1, providing for automatic style formatting.

5. The system according to claim 1, wherein the representation of information inserted into the structured data element of the structured document comprises a text field of the structured data element with text comprising at least part of the representation of information inserted into the associated part of the report.

6. The system according to claim 1, further comprising
a copy preparation unit for determining at least one of a to-be-copied structured data element of the structured document and a to-be-copied part of the report; and
a copy execution unit for inserting a corresponding representation of information into the other one of the structured document and the report, wherein the corresponding representation of information corresponds to information represented by said at least one of the to-be-copied structured data element and the to-be-copied part of the report;
wherein the associating unit is arranged for associating said at least one of the to-be-copied structured data element of the structured document and the to-be-copied part of the report with the corresponding representation inserted into the other one of the structured document and the report.

7. The system according to claim 1, wherein the associating unit is arranged for associating a plurality of structured data elements of the structured document with associated parts of the report, to obtain a correspondence mapping.

8. The system according claim 1, wherein the structured data element represents a standard term by means of a code.

9. A workstation comprising the system according to claim 1.

10. The system according to claim 1, wherein when an automatically generated free text is extended by a radiologist with dictated or otherwise edited text, identical style guidelines are used and a natural language text is structured and re-phrased using a set of predefined macro's to stimulate the use of one style.

11. A method of providing assistance with reporting, comprising;
with one or more computer processors, associating a structured data element of a structured document with an associated part of a report, wherein the report comprises text in a natural language, and wherein information represented by the structured data element corresponds to information represented by the associated part of the report;
with the one or more computer processors, determining a change to one of the structured data element and the associated part of the report, to obtain a determined change; and
with the one or more computer processors, making a corresponding change to the other one of the structured data element and the associated part of the report, based on the determined change,
wherein the determined change includes inserting a representation of information into the one of the structured data element of the structured document and the associated part of the report, and
wherein making the corresponding change includes inserting a corresponding representation of information into the other one of the structured data element and the associated part of the report, and
wherein making the corresponding change includes converting the inserted representation of information, being a new structured data element, by applying natural language generation to generate a piece of natural language suitable for insertion into the associated part of the report.

12. A non-transitory computer-readable medium carrying software instructions for causing a processor system to perform the method according to claim 11.

13. A workstation including one or more computer processors programmed to perform the method according to claim 11.

14. A system for providing assistance with reporting, comprising:
one or more computer processors configured to:
associate a structure data element of a structured document with an associated part of a report, the report including text in a natural language, and the structured data element represents information corresponding to information represented by the associated part of the report,
determine a change to one of the structured data element and the associated part of the report, to obtain a determined change including:
inserting a representation of information into the one of the structured data element of the structured document and the associated part of the report; and
make a corresponding change to the other one of the structured data element and the associated part of the report, based on the determined change including:
inserting a corresponding representation of information into the other one of the structured data element and the associated part of the report, and
converting the inserted representation of information, being a new structured data element, by applying natural language generation to generate a piece of natural language suitable for insertion into the associated part of the report.

15. The system according to claim 14, wherein the one or more computer processors are further configured to:
determine a first cursor position in one of the structured document and the report; and
determine a second cursor position in the other one of the structured document and the report, wherein the first cursor position and the second cursor position point to the structured data element and the associated part of the report.

16. The system according to claim 14, wherein the one or more processors are further configured to:
determine at least one of a to-be-copied structured data element of the structured document and a to-be-copied part of the report; and
insert a corresponding representation of information into the other one of the structured document and the report, the corresponding representation of information corresponding to information represented by said at least one of the to-be-copied structure data element and the to-be-copied part of the report;

wherein the associating includes associating said at least one of the to-be-copied structured data element of the structured document and the to-be-copied part of the report with the corresponding representation inserted into the other one of the structured documents and the report.

* * * * *